United States Patent [19]

Stacey et al.

[11] Patent Number: 5,173,424

[45] Date of Patent: Dec. 22, 1992

[54] **ENHANCING MODULATION ABILITY OF *RHIZOBIUM JAPONICUM* BY INCUBATION WITH SOYBEAN LECTIN**

[75] Inventors: Gary Stacey; Larry J. Halverson, both of Knoxville, Tenn.; Robert M. Zablotowicz, Syracuse, N.Y.

[73] Assignee: LiphaTech, Inc., Milwaukee, Wis.

[21] Appl. No.: 266,267

[22] Filed: Oct. 26, 1988

Related U.S. Application Data

[63] Continuation of Ser. No. 163,151, Feb. 26, 1988, abandoned, which is a continuation of Ser. No. 636,897, Aug. 2, 1984, abandoned.

[51] Int. Cl.$^5$ .................. C12N 1/20; C12N 11/00; C05F 11/08; C12R 1/41
[52] U.S. Cl. .................. 435/252.2; 71/7; 435/174; 435/878
[58] Field of Search ............... 435/174, 177, 253, 254, 435/878, 71, 252.2

[56] References Cited

U.S. PATENT DOCUMENTS 3,616,236 10/1971 Delin .......................... 435/878 X
4,434,231  2/1984 Jung ........................... 435/878 X

OTHER PUBLICATIONS

Dazzo, et al., Applied and Environmental Microbiology, vol. 32, No. 1, 1976, pp. 166–171.
Dazzo, et al., Applied Microbiology, vol. 30, No. 6, 1975, pp. 1017–1033.
Buhlool, et al., Journal of Bacteriology, vol. 125, No. 3, 1976, pp. 1188–1194.
Su et al., Biochmica et Biophysica Acta 629 (1980) 292–304.
Goldberg et al., *Cell*, vol. 33, 465–475, Jun. 1983.
Pull et al., *Science*, vol. 200, pp. 1277–1279, Jun. 16, 1978.
Bhagwat, et al., "Legume–Rhizobium Interactions: Cowpea Root Exudate Elicits Faster Nodulation Response By Rhizobium Species" Applied and Environmental Biology, 800–05 (1982).
Halverson, et al., "Host Recognition In The Rhizobium–Soybean Symbiosis", Plant Physiology, 77, 621–25 (1985).
Stacey, et al., "Host Recognition In The Rhizobium–Soybean Symbiosis", Plant Physiology, 66, 609–14 (1980).
Halverson, et al., "Effect Of Lectin On Nodulation By Wild-Type Bradyrhizobium Japonicum And A Nodulation-Defective Mutant", Applied and Environmental Microbiology, 753–60 (Apr. 1986).
Bhuvaneswari, et al., "Role Of Lectins In Plant Microorganism Interactions", Plant Physiology, 62, 71–74 (1978).
Bhuvaneswari, et al., "Role Of Lectins In Plant-Microorganism Interactions", Plant Physiology, 60, 486–91 (1977).
Halverson, et al., "Host Recognition In The Rhizobium–Soybean Symbiosis", Plant Physiology, 74, 84–89 (1984).
Halverson and Stacey, Mutants of Rhizobium Japonicum Defective in Nodule Initiation, "Plant Physiology Supplement," vol. 72, NO. 1, p. 25, May 1983.
Gade, et al., The Isolation and Characterization of a Root Lectin From Soybean, "Journal of Biological Chemistry," vol. 256, No. 24, Dec. 25, pp. 12,905–12,910, 1981.

*Primary Examiner*—David M. Naff
*Attorney, Agent, or Firm*—Foley & Lardner

[57] ABSTRACT

The nodulation ability and/or competition characteristics of strains of *Rhizobium japonicum* is enhanced by incubating the strains in a nodulation and/or competitive enhancing effective amount of one or more soybean lectins, or in composition comprising a nodulation and/or competitiveness enhancing effective amount of such lectins such as soybean seed exudate. An inoculum can be prepared containing a carrier, *Rhizobium japonicum* and lectin.

2 Claims, 4 Drawing Sheets

ENHANCING MODULATION ABILITY OF *RHIZOBIUM JAPONICUM* BY INCUBATION WITH SOYBEAN LECTIN

This application is a continuation of U.S. patent application Ser. No. 163,151, filed Feb. 26, 1988, abandoned, which is continuation of U.S. patent application Ser. No. 636,897, filed Aug. 2, 1984, abandoned.

BACKGROUND OF THE INVENTION

1. Field of the Invention

This invention relates to a method of enhancing the nodulation ability and/or the competitive characteristics of strains of *Rhizobium japonicum*. More particularly, this invention relates to such a method in which said strains are incubated in the presence of soybean root exudate, soybean lectins, a composition comprising said lectin and/or root exudate or a combination thereof.

2. Description of the Prior Art

The process of biological nitrogen fixation consists of the reduction of elementary nitrogen to ammonia by living organisms. This biologically fixed nitrogen is the major source of nitrogen available for the formation of protein, which is essential in maintaining the world food supply. The economic importance of biological nitrogen fixation on the Earth cannot be over emphasized. It has been reported that nitrogen fixation by all biological organisms accounts for 80 percent of the nitrogen fixed on Earth per year. Leguminous and nonleguminous symbionts alone account for about 5.5 million tons of nitrogen fixed per year in the United States. About 13,000 species of leguminous plants exist, the vast majority of which are involved in a symbiotic relationship with nitrogen fixing bacteria. Some of the economically more important legumes include soybean, peas, clover and the like. As a result of increased world population there has been increased activity in enhancement of world food sources. One food crop which in recent years has received ever increasing emphasis is soybean because of its high protein content. Much of the enhanced protein content of soybean results from the superior nitrogen fixing capabilities of *Rhizobium japonicum*, the nitrogen fixing bacteria associated with soybean.

The establishment of a nitrogen fixing symbiosis in leguminous plants is a complex process involving physiological logical and biochemical properties of both the bacterium and host plant. The interaction of a particular legume species with its respective Rhizobium symbiont is known to be fairly specific. This has led to the establishment of cross-inoculation groups: that is, *R. phaseoli-bean*, *R. trifolii-clover*, *R. meliloti-alfalfa*, *R. leguminosarum-pea*, and *R. japonicum-soybean*. The underlying molecular mechanism to explain this infection specificity is presently an area of intense investigation. Lectins, proteins that bind carbohydrates, have been implicated as important in determining Rhizobium host specificity. According to this hypothesis, host-plants lectins located on the root surface recognize carbohydrate receptors on the compatible Rhizobium cell surface and, thereby, bind the bacteria to the root. This hypothesis was first proposed after demonstrating the specific binding of soybean lectin to *Rhizobium japonicum* but not to other incompatible Rhizobium species.

It has been demonstrated that nodulation on the roots of soybean and cowpea is developmentally restricted to the area between the root tip (RT) and smallest emergent root hair (SERH) observable with a dissecting microscope. Host root cells within this region become progressively less susceptible to nodulation as the root grows with successful nodulation occurring in this zone no later than four hours after inoculation. This time limit for the initiation of nodules within the RT-SERH zone enables one to infer the relative rate of infection by the position of the uppermost nodule as measured from the RT mark made at the time of inoculation.

To one skilled in the art, many *R. japonicum* strains of superior nitrogen fixation efficiency are available. Many of these strains, although efficient nitrogen fixers are of limited ability as they are unable to establish as nodule occupants in soil containing indigenous populations of rhizobia. The ability to improve the competitiveness to realize the maximum normal rhizobia is necessary to realize the maximum benefits of the Rhizobium symbiosis.

There is therefore a need to establish a method or composition which is capable of enhancing the nodulation ability and competitiveness of strains of *Rhizobium japonicum*.

SUMMARY OF THE INVENTION

This invention relates to a method of enhancing the nodulating ability and/or competitiveness of strains of *Rhizobium japonicum*. More particularly, this invention relates to a method of enhancing such nodulating ability and/or competitiveness by incubating said *Rhizobium japonicum* with "a nodulation and/or competitiveness enhancing effective amount" of one or more "soybean lectins" prior to inoculation. Another aspect of this invention relates to strains of *R. japonicum* which have been incubated with one or more soybean lectins, which exhibit enhanced nodulation and/or competitiveness characteristics. Yet another aspect of this invention relates to an inoculum comprising an effective carrier, a strain of *Rhizobium japonicum* and "a nodulation and/or competitiveness enhancing effective amount" of one or more said lectins.

DESCRIPTION OF THE PREFERRED EMBODIMENTS

In the process of this invention a culture or collection comprising a strain of *R. japonicum* is incubated with "a nodulation and/or competitiveness enhancing effective amount" of one or more "soybean lectins" or a composition comprising said lectins by admixture or otherwise. As used herein "soybean lectins" are defined as proteins having the ability to bind to N-acetyl-D-galactosamine, galactose, or polymers or macromolecules containing these sugars. Soybean lectin can be isolated from the root of the soybean plant, soybean seeds, stems of such plants and from plant leaves. The particular soybean lectin employed is not critical. In the preferred embodiments of the invention, however, lectins derived from soybean seeds and roots are employed and in the particularly preferred embodiments lectins isolated from soybean roots are preferred. Such lectins can be obtained from commercial sources, isolated and used in pure form or crude mixtures containing one or more of the lectins can be used. For example, soybean lectins from the roots of soybean plant can be isolated as an impure aqueous root exudate. This aqueous root exudate which contains varying amounts of the soybean root lectin can be used in the method of this invention. The soybean lectins and/or soybean root exudate can also be included in the carrier of the inoculum used to inoculate the soybean seed. For example, such pure or impure lectins and/or root or seed exudate can be combined with a traditional carrier, as for example peat moss, clays, and the like, and the desired strain of *Rhizobium japonicum* to form a superior innoculum for soybean. This composition can be used immediately after preparation or can be stored for years until used. Alternatively, the strain of *Rhizobium japonicum* can be incubated prior to inclusion in such an innoculum which may or may not contain the pure or impure soybean lectins or compositions comprising same.

The particular strain of *Rhizobium japonicum* treated by the lectins is not critical, and can vary widely. Such strains can be effective nodulators, ineffective nodulators, or strains which have relatively normal nodulating abilities, or such strains can exhibit superior competitive characteristics, normal competitive characteristics or ineffective competitive characteristics. Illustrative of strains of *R. japonicum* which can be treated in the process of this invention are strains 3I1b110, 61A76, HS111, SM1, I-110, and the like.

The strains of *R. japonicum* are treated with a "nodulation and/or competitiveness enhancing amount" of one or more soybean lectins or a composition comprising one or more of said lectins. As used herein, a "nodulation and/or competitiveness enhancing effective amount" is an amount of such lectins which is capable of enhancing the nodulation abilities and/or the competitiveness of the strain to any extent. As is apparent this amount can vary widely over a broad range. However, in general, the amount of such lectins employed is usually at least about 4 pg/ml. The upper amount of lectins employed is not critical in that these materials are generally not toxic to the *R. japonicum* or plant at very high concentrations. In the preferred embodiments of the invention, the amount of lectins employed is from about 4 pg/ml to about 100 $\mu$g/ml, and in the particularly preferred embodiments if from about 500 pg/ml to about 50 ug/ml. Amongst these particularly preferred embodiments, most preferred are those embodiments in which the amount of lectin employed is from about 1 $\mu$g/ml to about 15 $\mu$g/ml.

The one or more lectins, and the strain of *R. japonicum* are generally contacted in an acceptable carrier which is solvent system which is capable of solvating a nodulating and/or competitiveness enhancing effective amount of said one or more lectins to some extent, and which does not adversely affect the strain of *R. japonicum*. In the preferred embodiments of the invention the contacting solvent is water.

The duration of the incubation period can vary widely, the only requirement being that the duration of such period is sufficient for the nodulation ability and/or competitiveness of the strain to be enhanced to any extent. In general, the incubation period is at least about 0.5 hour (h). In the preferred embodiments of the invention, the incubation period is at least about 1 h, and in the particularly preferred embodiments is at least about 24 h. Amongst these particularly preferred embodiments most preferred are those embodiments in which the incubation period is at least about 72 h.

The strain of *R. japonicum* is incubated in the presence of the soybean lectin usually at autogenous pressure, and at a temperature which will not adversely affect the strain. Usually, the incubation is carried out at a temperature at which the strain of *R. japonicum* is capable of growth, usually at a temperature of from about 25° C. to about 30° C.

The process of this invention is useful for the development or preparation of strains of *R. japonicum* which have enhanced nodulation abilities and/or superior competitive characteristics. It is believed that these abilities are reflected in enhanced competitive qualities and nodule occupancies of strains of *R. japonicum* treated in accordance with this invention and in enhanced soybean yields resulting from use of such treated strains.

The following specific examples are presented to more particularly illustrate the invention.

EXAMPLE I (A) Growth of Plants for Collection of Root Exudates

Soybean (Glycine Max L. Merr) cv Essex seeds obtained from D. R. Mayo Seed Co., Knoxville, Tenn. were surface sterilized using the procedure of Wacek, T. J., W. J. Brill, "Simple Rapid Assay for Screening Nitrogen Fixing Ability in Soybean", *Crop Sci.*, 15:519-523 (1976). Sterilized seeds were germinated on sterile moist filter paper in petri plates for two days in the dark at room temperature.

Aseptically germinated seedlings, as described above, were affixed atop of a sterile fluted filter paper (1.3 cm $\times$ 8.9 cm) inside a 45 ml serum vial containing 15 ml of sterile half-strength plant nutrient solution (PNS) which is an aqueous solution containing $CaSO_4 \cdot 2H_2O$ (0.002M); $K_2SO_4$ ($5 \times 10^{-3}$M); $MgSO_4 \cdot 7H_2O$ ($5 \times 10^{-4}$M); NaFe-EDTA ($4 \times 10^{-5}$M); $CoCl_2 \cdot 6H_2O$ ($5.3 \times 10^{-7}$M), $Na_2HPO_4 \cdot H_2O$ ($5 \times 10^{-3}$M); $MnSO_4 \cdot H_2O$ ($5 \times 10^{-6}$M); $CuSO_4 \cdot 5H_2O$ ($5 \times 10^{-7}$M); $ZnSO_4 \cdot 7H_2O$ ($2 \times 10^{-6}$M); KCl ($5 \times 10^{-5}$M); $H_3BO_3$ ($25 \times 10^{-6}$M); and $(NH_4)_6Mo_7O_{24} \cdot 4H_2O$ ($1.5 \times 10^{-8}$M). A sterile 18 oz. Whirlpac plastic bag (Nasco, Inc., Oakville, Conn.) was placed over the vial, and the vial was placed on a light table. The seedlings were maintained hydroponically for ten days on the light table at 26° C. and 160 $\mu$E m$^{-2}$ sec$^{-1}$ with a 14 h photoperiod. Plants free of visible microbial contamination after ten days of growth were used to collect the half-strength PNS containing the root exudate. Root exudate was filter sterilized (0.45 $\mu$m filters, Nalge Co., Rochester, N.Y.) and used immediately.

(B) Rhizobium Culture and Rhizobium Pretreatment

*Rhizobium japonicum* used in the experiment was strain 110, which is colony type I110 isolated from wildtype strain 3I1b110 (mutant prefix HS) and obtained from G. H. Elkan (North Carolina State University, Raleigh, N.C.). Isolation of mutant strain HS111 and partial characterization of its slow-to-nodulate phenotype was reported previously in Stacey, et al. "Mutants of *Rhizobium japonicum* defective in nodulation", Arch. Microbiol., 132:219–224 (1982). *Rhizobium japonicum* colony-type SM of wild type strain 61A76 has been described previously by Maier and Brill (J. Bacterial 127:763–769 (1976)). However, strain $SM_1$ will nodulate if given sufficient time to do so and has been reclassified as a slow-to-nodulate mutant (Arch. Microbiol. 132 219–224 (1982)).

*Rhizobium japonicum* cultures were prepared as described above. Cell suspensions were added to root exudate or PNS in which plants had not been grown. Ten milliliters of the $2 \times 10^9$ cells/ml suspension were aseptically added to 50 ml of root exudate or half-strength PNS in 250 ml Erlenmeyer flasks and incubated at 30° C. without shaking for 6 to 72 h. Following the desired incubation time, the cell suspension was pelleted in sterile centrifuge tubes at $7,000 \times$ g for 10 minutes, washed once with sterile half-strength PNS, and resuspended to the original volume with sterile half-strength PNS. Plate counts performed at various times during preincubation indicated that cell numbers did not change during incubation.

(C) Preparation of Inocula

Stock cultures were maintained on yeast-extract mannitol (YEM) agar as described in Stacey, G., et al., Host Recognition in the Rhizobium—soybean symboisis, *Plant Physiol.*, 66:609–614 (1980). Single cell colonies from the stock cultures were used to inoculate 50 ml of AMA broth in 250 ml Erlenmeyer flasks. These cultures were maintained on a rotary shaker at 30° C. for 3.5 days (mid-log phase). Cultures were harvested by centrifugation at $7,000 \times$ g for 10 min in sterile centrifuge tubes, washed once with 20 ml of sterile half-strength PNS to a cell density of either $1 \times 10^8$ cells/ml (Bhuvaneswari; T. V., et al., *Plant Physiol.* 66:1027–1031 (1980)) or $2 \times 10^9$ cells/ml (Bhuvaneswari, T. V., et al., Plant Physiol, 62:71–74 (1978)). Aliquots of such suspensions were used to inoculate plants directly ($1 \times 10^8$ cells/ml) or for pretreatment incubations ($2 \times 10^9$ cells/ml).

(D) Growth of Seedlings and Inoculation

Seeds were surface sterilized as described previously. Sterilized seeds were germinated on sterile moist filler paper in petri plates for two days in the dark at room temperature. Seedlings were then transferred aseptically to clear plastic growth pouches (diSPo Seed-Pack, Northrup King Seed Co., Minneapolis, Minn.). Plastic growth pouches had previously been moistened with 10 ml of half-strength PNS and autoclaved. Three seedlings were grown in each pouch.

Seedlings were maintained in a growth chamber under the following conditions: 70% relative humidity; 20°–23° C.; light intensity 380 $\mu E\ m^{-2}\ sec^{-1}$ with a 14 h photoperiod. The plastic pouches were watered as needed with half-strength PNS. The positions of the root tip (RT) and smallest emerging root hair (SERH) of 3 day old seedlings were marked on the surface of the growth pouches with the aid of a dissecting microscope (5). The entire root of each seedling was inoculated with 1.0 ml of a $1 \times 10^8$ cells/ml suspension. Uninoculated pouches were included with each experiment to monitor for contamination.

(E) Scoring of Nodulation

Plants inoculated with the wild type *R. japonicum* strains 110 and 61A76 were scored 14 days after inoculation and the slow-to-nodulate mutants, strains HS111 and $SM_1$, were scored 28 days after inoculation. The position of all nodules on the primary root was measured relative to the RT mark made at the time of inoculation to the nearest 0.1 mm. The relative distances of each nodule on the primary root from the RT mark was calculated as a percentage of the RT-SERH distance of a given plant.

Figure 1:
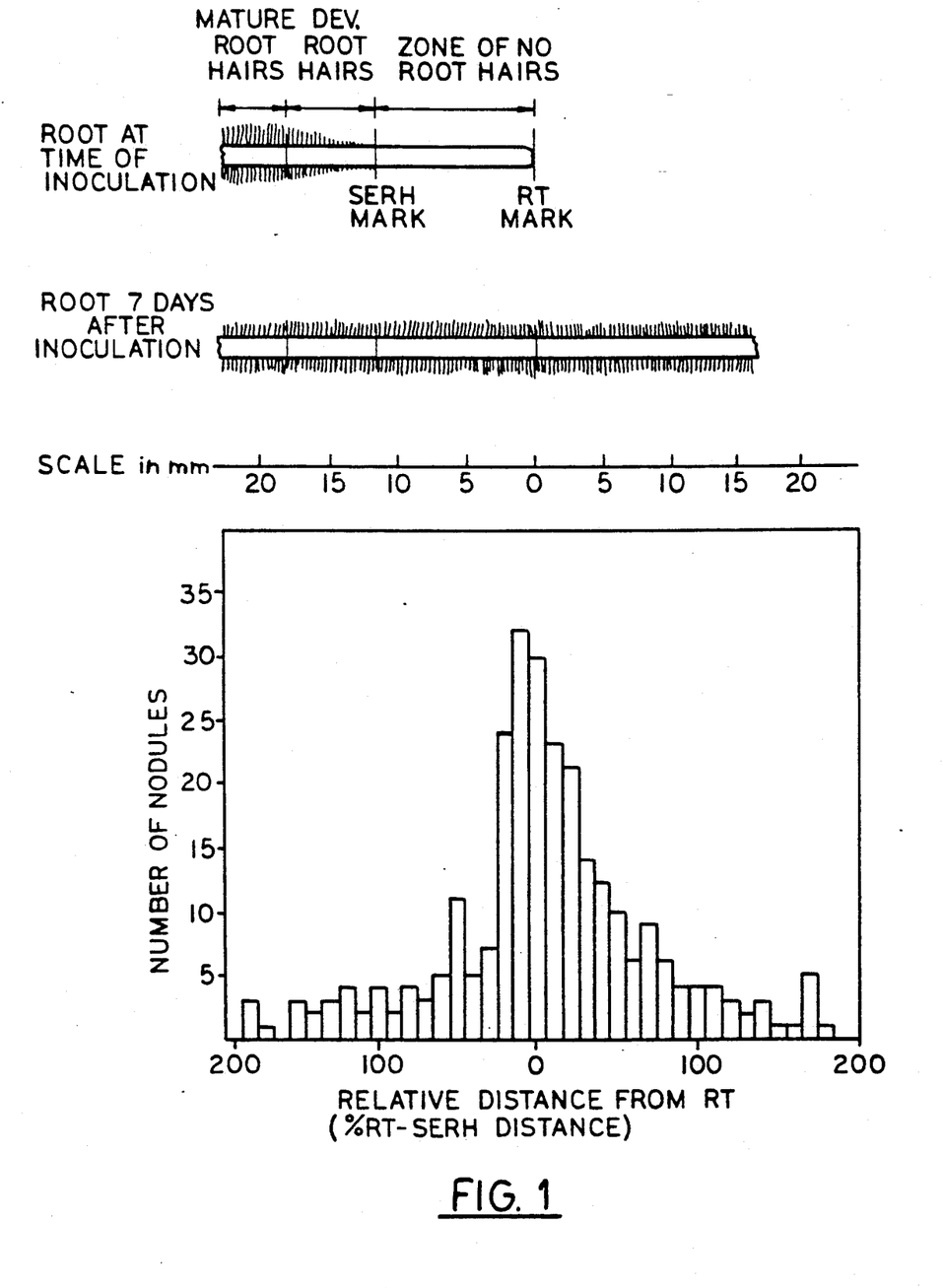
FIG. 1 is a diagramatic representation of a soybean root at the time of inoculation and after seven days of root development and the profile of the distribution of nodules formed by *R. japonicum* strain 311b110.

The nodulation profile of the wild type *R. japonicum* strain 110 is shown in FIG. I. The relative distance of each nodule on the primary root from the root tip (RT) mark was calculated as a percentage of the RT to smallest emerging root hair (SERH) distance for a given plant. Zero percent corresponds to the position of the RT and 100 percent to the position of the SERH at the time of inoculation. *R. japonicum* strain 110 demonstrates a maximum frequency of nodulation in the range of $+30$ to $-60\%$ of the RT-SERH distance from the RT mark.

Figure 2:
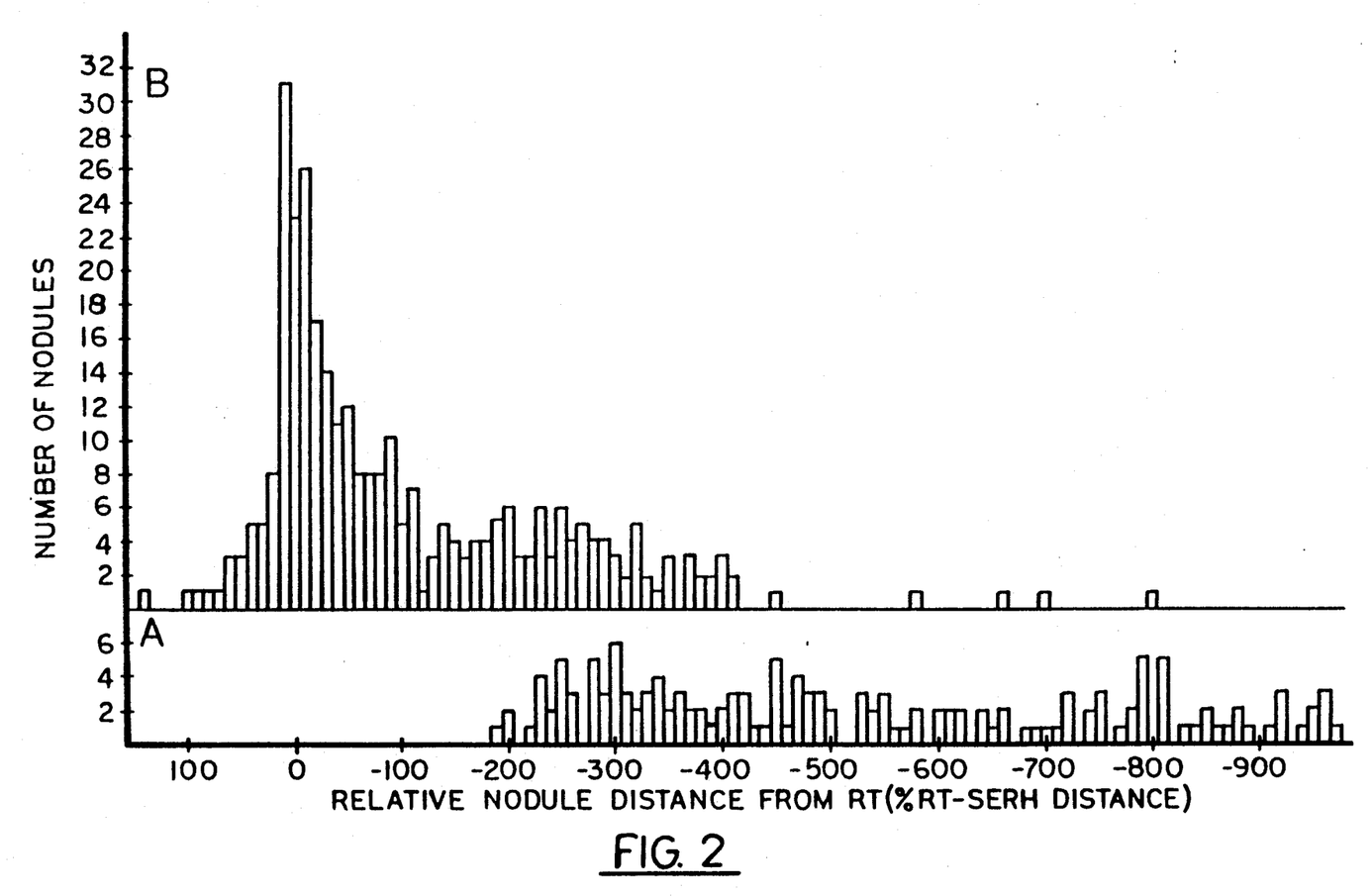
FIG. 2 is a profile of the distribution of nodules formed on soybean (G. Max L. Merr) cv. Essex after inoculation with the slow-to-nodulate mutant strain HS 111 (A) and strain HS 111 after preincubation in soybean root exudate (B).

In contrast to the wild type, the nodulation profile of the slow-to-nodulate mutant strain HS111 shows a broad scatter of nodulation in the range of $-200$ to $-1000\%$ of the RT-SERH distance as measured from the RT mark (FIG. 2A). The average distance of the uppermost nodule is $55.9 \pm 2.2$ mm below the RT mark made at the time of inoculation. The number of nodules per plant produced by strain HS111 ($2.6 \pm 1.1$) is less than half of that produced by the wildtype strain 110 ($7.6 \pm 3.7$). Nodules produced by strain HS111 became visible within 22–24 days after inoculation compared to 10–12 days for the wild type strain 110. The fact that the average position of the uppermost nodule for strain HS111 is far below that of the wild type suggests that this mutant is defective in the initiation of infection. Seedlings in these experiments grow at a rate of approximately 1.0 mm/h. Therefore it takes approximately 56 h for strain HS111 to initiate an infection in the RT-SERH zone.

FIG. 2B shows the nodulation profile of strain HS111 preincubated in soybean root exudates for 72 h. The nodulation profile is shifted and similar to that of the wild type strain 110 exhibiting a maximum frequency of nodulation in the range of $+20$ to $-100\%$ of the RT-SERH distance from the RT marked at the time of inoculation. The average distance of the uppermost nodule has shifted from $55.9 \pm 2.2$ mm below the RT mark (i.e., when not preincubated in soybean root exudate) to $0.8 \pm 1.1$ mm below the RT mark. In addition to the upward shift in the nodulation profile and average position of the uppermost nodule from the RT mark, there is an increase in the number of nodules formed by strain HS111 from $2.6 \pm 1.1$ to $4.8 \pm 2.0$ nodules per plant after preincubation in root exudate. Preincubation in soybean root exudate apparently enables strain HS111 to overcome its inability to initiate an infection at a rate comparable to the wildtype.

In the following Table I is set forth data showing the effect of Rhizobium pretreatment or nodulation characteristics.

TABLE I

| Rhizobium Strain | Average Distance of Uppermost Nodule (mm) | % Nodulation Only Below RT Mark |
|---|---|---|
| 3Ilb110 | 2.3 ± 0.9 | 33 |
| 3Ilb110 PNSa | 0.9 ± 1.0 | 28 |
| 3Ilb110 RE[b] | 1.0 ± 0.3 | 18 |
| HS111 | −55 ± 2.2 | 100 |
| HS111 PNS | −51.7 ± 2.8 | 100 |
| HS111 RE | −0.8 ± 1.7 | 37 |
| 61A76 | 0.4 ± 0.5 | 32 |
| $SM_1$ | 1.1 ± 0.8 | 22 |

[a]Preincubated in plant nutrient solution (PNS) for 72 h prior to inoculation.
[b]Preincubated in soybean exudate (RE) for 72 h prior to inoculation.

As shown in Table I, inoculation of G. max cv. Essex with R. japonicum strain 110 or 61A76 usually yields nodules above the RT mark. The average distance of the uppermost nodule found on plants inoculated with strain 110 cells is 2.3±0.9 mm above the RT mark made at the time of inoculation and 67% of the plants nodulate above the RT mark. Similar results were seen for strain 61A76, with the average distance of the uppermost nodule being 0.4±5 mm above the RT mark made at the time of inoculation and 68% of the plants nodulate above the RT mark. In contrast, plants inoculated with strain HS111 nodulate only below the RT mark (100%) with the average distance of the uppermost nodule being 55.9±2.2 mm below the RT mark made at the time of inoculation. With the slow-to-nodulate mutant strain $SM_1$ (derived from wild type strain 61A76, 14) the average position of the uppermost nodule is 1.1±0.8 mm above the RT mark made at the time of inoculation and 78% of the plants nodulate above the RT mark. Thus, not all slow-to-nodulate mutants exhibit a similar nodulation phenotype to strain HS111. The slow-to-nodulate mutant strain $SM_1$ is apparently defective in the rate of nodule formation rather than in the initiation of an infection.

Preincubation of the slow-to-nodulate strain HS111 in soybean root exudate for 72 h results in nodulation generally above the RT mark (63%). As a control, strain HS111 was preincubated in PNS in which plants had not been grown. Essentially no difference was seen in the nodulating characteristics of strain HS111 preincubated in PNS or taken directly from YEM medium. In both cases, all plants nodulate only below the RT mark made at the time of inoculation. Preincubation of the wild type strain 110 in soybean root exudate or PNS gave no significant change in its nodulation characteristics.

Figure 3:
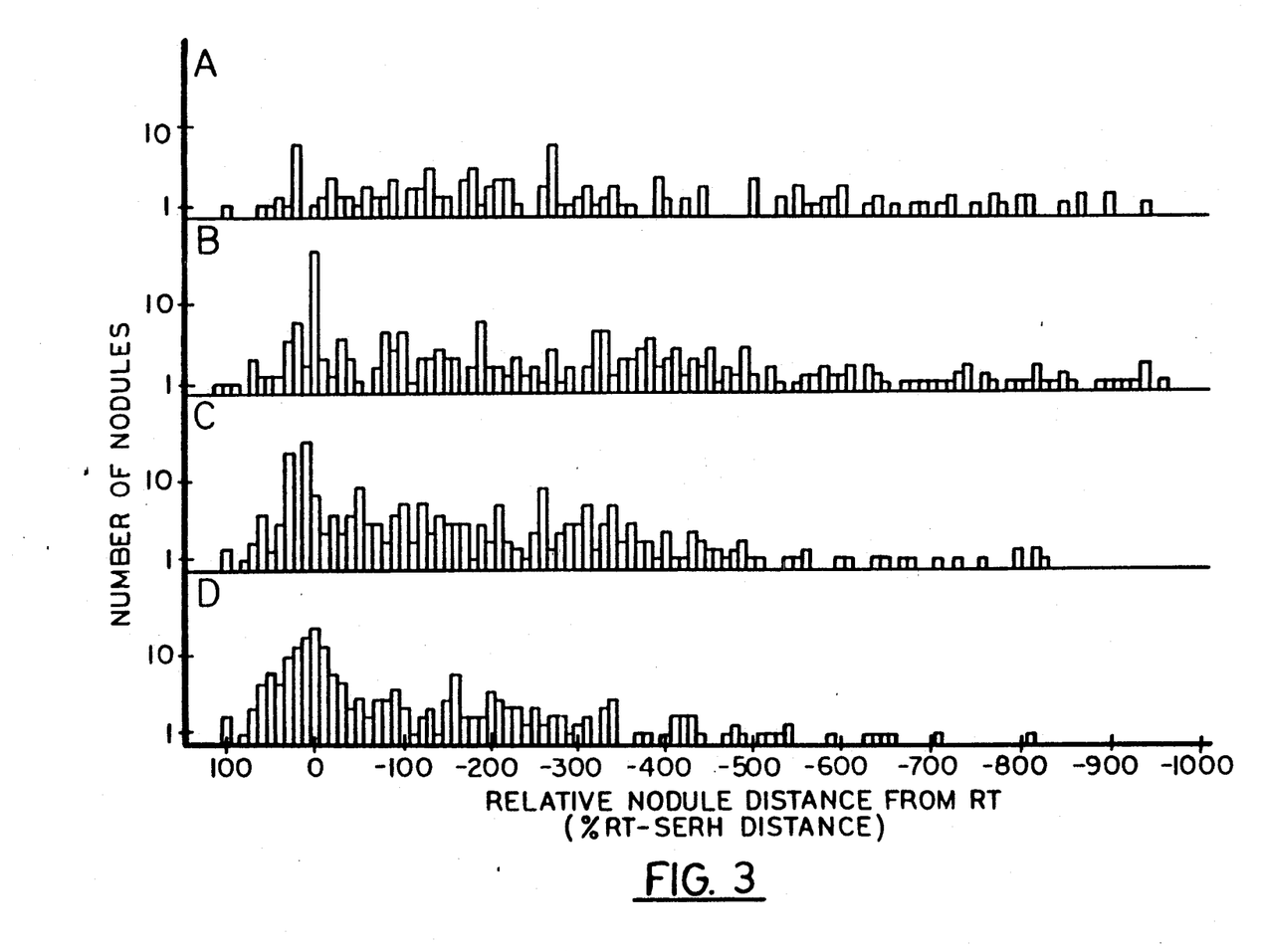
FIG. 3 is a profile of the distribution of nodules formed on seedlings of soybean (G. Max L. Merr) cv. Essex inoculated with the slow-to-nodulate mutant strain HS111 (A) and strain HS111 preincubated in soybean root exudate for 12 hours (B), 24 hrs (C) and 72 hrs (D).
Figure 4:
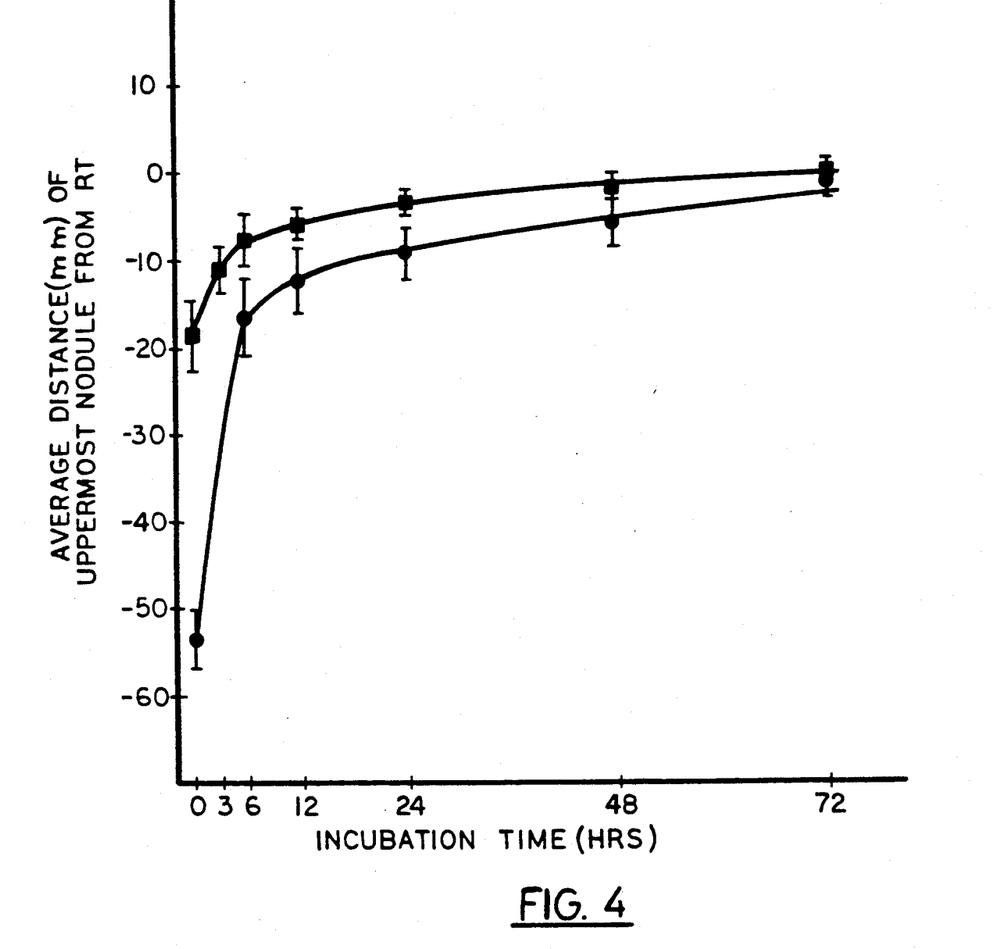
FIG. 4 depicts the relationship between the time of incubation in soybean exudate and the nodulation response by the slow-to-nodulate *R. japonicum* mutant strain HS111 on seedlings and seed lots of G. Max. cv. Essex.

To determine the critical time necessary for strain HS111 to interact with root exudate a time course study was performed the results of which are set forth in FIGS. 3 and 4. FIG. 3 shows the nodulation profiles of strain HS111 preincubated in soybean root exudate over a period of 72 h and inoculated onto 3 days old G. max. cv. Essex (1982 seed lot) seedlings. The nodulation profile at 0 h shows a broad scatter of nodulation similar to that seen for the 1981 Essex seed lot but in the range of +100 to −900 (1982) compared to −200 to −1000% (1981) of the RT-SERH distance as measured from the RT mark made at the time of inoculation (Panel 3A). However, by 12 h (Panel 3B) there is an increase in the frequency of nodulation near the RT mark and by 48 h (Panel 3C) the profile is beginning to resemble the profile seen after 72 h of incubation (Panel 3D). The nodulation profile of strain HS111 after 72 h of incubation in root exudate demonstrates a maximum frequency of nodulation in the range of +80 to −100% of the RT-SERH distance as measured from the RT mark made at the time of inoculation. The average distance of the uppermost nodule is shifted from 18.4±4.0 mm below the RT mark at 0 h, to 5.7±1.8 mm below the RT mark by 12 h, to 1.6±1.6 mm below the RT mark by 48 h, and, finally after 72 h of incubation in root exudate, to 0.2±1.2 mm above the RT mark made at the time of inoculation. This shift in nodulation characteristics can also be seen in the percent of nodules appearing only below the RT mark. At 0 h, 60% of the plants nodulated only below the RT mark, at 12 h 40%, at 48 h 34%, and at 72 h 24% of the nodules appeared only below the RT mark made at the time of inoculation. Under similar circumstances the wild type R. japonicum strain 110 had an average distance of the uppermost nodule of 3.5±0.3 mm above the RT mark made at the time of inoculation. FIG. 4 shows a graphic representation of the data from FIG. 3 and a time course for inoculation of strain HS111 onto 1981 Essex seeds. For the 1981 Essex seeds, at 0 time the average position of the uppermost nodule was 51.7±2.8 mm below the RT mark made at the time of inoculation. However, by 6 h the position of the uppermost nodule was 12.5±2.8 mm below the RT mark and at 72 h the uppermost nodule was near the RT mark made at the time of inoculation. A similar behavior was observed with the 1982 Essex seed lot (as shown in FIG. 4). Statistical analysis of the data in FIG. 4 demonstrated a significant difference between 0 h and 72 h data points at a p=0.2 confidence level for both the 1981 and 1982 seed lots of G. max cv. Essex. The half-time for the maximum response of strain HS111 to incubation in root exudate is less than 6 h, which is less than a single generation time for R. japonicum.

This effect of preincubation could be due to two possibilities; one, that preincubation selects for cells that have undergone a genotypic change or, two, that the enhancement of nodule initiation is due to a phenotypic reversal of the mutation. To distinguish between these two possibilities, bacteria were isolated from nodules produced by strain HS111 after 72 h of preincubation in root exudate.

Nodules were aseptically removed from the primary root, rinsed in 70% EtOH for a few seconds, washed twice in sterile distilled water and immersed in 0.1% $HgCl_2$ in 0.06N HCl for 5 minutes. Following this treatment, nodules were washed 5 times in sterile distilled water and crushed in 0.5 ml of AMA broth. Nodule isolates were then streaked onto AMA agar and incubated at 30° C. Single colony isolates were grown in AMA broth and prepared for inoculation of seedlings as described previously.

Nodules were taken from various points along the primary root above and below the RT mark made at the time of inoculation. Soybean seedlings were infected with cultures of these isolates to determine if they would nodulate approximately 18 mm below the RT mark or near the RT mark made at the time of inoculation. In all cases the nodule isolates nodulated, on the average, 18 mm below the RT mark. This indicates that the change in nodulation characteristics of strain HS111 produced by preincubation in soybean root exudate is due to a phenotypic reversal rather than a genotypic reversion of the mutant characteristic.

During preincubation in root exudate, Rhizobium cultures are not shaken. It is conceivable that this static growth condition could cause changes in the cells of strain HS111 that would lead to changes in the nodulation profile. To test for this possibility, seedlings were inoculated with cells of strain HS111 grown in YEM media in which the culture was not shaken. Strain HS111 grown in static culture nodulated 15.8±2.6 mm below the RT mark made at the time of inoculation indicating that the static culture conditions alone are insufficient to induce the enhancement of nodule initiation.

(F) Characterization of the nodulation enhancing factor(s) found in soybean root exudate Various pretreatments of the root exudate prior to Rhizobium inoculation were done to ascertain the nature of the active nodulation enhancing component(s) of soybean root exudate. To determine if the active factor(s) of root exudate was protein in nature, the root exudate was boiled for 30 min. or treated with trypsin for 5 h as follows:

Aseptically collected root exudate or filter sterilized half-strength PNS was swirled gently with 1.0 ml of trypsin covalently bound to Sepharose beads (50 units of activity/ml) or 2 grams of Sepharose 4B (both from Sigma Chemical Co. St. Louis, Mo.) for 5 hr in a 30° C. water bath. These solutions were then filtered through a sintered glass filter to remove the Sepharose beads and filter-sterilized. One mg of trypsin inhibitor (Sigma Chemical Co.) was then added to each 50 ml aliquot of root exudate or PNS. One mg of trypsin inhibitor can inhibit 10,000 units of trypsin according to manufacturers specifications. No trypsin activity was detectable in the root exudates before trypsin addition or after the removal of the trypsin beads by filtration. Trypsin activity was measured by the hydrolysis of α-N-benzoyl-L-arginine ethyl ester as according to directions provided by Sigma Chemical Co.

Following soybean root exudate (RE) or PNS treatment, the slow-to-nodulate mutant HS111 was incubated in RE or PNS for 72 h prior to inoculation of 3 day old seedlings. The effect of the root exudate treatment on nodulation by mutant strain HS111 is set forth in the following Table II.

TABLE II

| Strain | Average Distance of Uppermost Nodule (mm) | % Nodulation Only Below RT Mark |
|---|---|---|
| PNS | −16.9 ± 3.1 | 83 |
| PNS-Trypsin | −15.7 ± 3.8 | 76 |
| RE-Sepharose | −1.3 ± 2.4 | 41 |
| RE-Boiled | −17.8 ± 2.9 | 78 |
| RE-Trypsin | −16.2 ± 3.1 | 83 |

As shown in Table II, after boiling and trypsin pretreatment, the average distance of the uppermost nodule is, respectively, 17.8±2.9 mm and 16.2±3.1 mm below the RT mark made at the time of inoculation. In both cases, the data in Table II shows that the percent of the nodules found only below the RT mark is significantly greater than for untreated root exudate or root exudate with Sepharose 4B beads and is comparable to that found with cells incubated in PNS. The protein concentration of the root exudate produced from seedlings of the 1981 and 1982 Essex cultivars was approximately 8 μg protein/ml as determined by the method of Bradford.

EXAMPLE II

The slow-to-nodulate strain HS111 was preincubated in 10 μg/ml soybean seed lectin (E.Y. Laboratories San Mateo, Calif.) in sterile-half-strength, PNS. Cultures were incubated in PNS, PNS/10 μg/ml Bovine Serum Albumin (BSA), the soybean root exudate (RE) of Example I and PNS/Soybean Seed Lectin (SBL) in a 30° C. incubator for 72 h or for 1 h prior to preparation for inoculating of 3 day old plants with a cell concentration of $1 \times 10^8$ cells/ml as described in Example I.

Cells incubated for 1 h were collected by centrifugation, washed with sterile half-strength PNS, centrifuged and re-suspended to volume with sterile half-strength PNS. These cells were then incubated for the duration of the 72 h incubation in sterile half-strength PNS prior to inoculation. The slow to nodulate mutants were scored after 28 days of growth. The results as set forth in the following Table III.

TABLE III

| PRE-TREAT-MENT | TIME OF INCUBA-TION (m) | AVERAGE DISTANCE OF UPPER-MOST NODULE FROM RT (MM) | % NODU-LATION ONLY BELOW RT |
|---|---|---|---|
| PNS | 72 | −16.2 ± 3.2 | 73 |
| PNS/BSA | 72 | −14.6 ± 2.4 | 73 |
| RE | 72 | −1.6 ± 1.9 | 39 |
| PNS/SBL | 72 | −2.9 ± 1.6 | 39 |
| PNS | 72 | −15.2 ± 2.7 | 74 |
| RE | 72 | −0.5 ± 1.4 | 34 |
| PNS/SBL | 72 | −0.9 ± 1.6 | 34 |
| PNS | 1 | −17.3 ± 2.6 | 64 |
| RE | 1 | −9.7 ± 3.0 | 56 |
| PNS/SBL | 1 | −8.0 ± 2.5 | 53 |

The results set forth in Table III show that pretreatment of mutant strain HS111 with soybean lectin (SBL) at the approximate protein concentration found in soybean root exudate (i.e., 10 μg/ml) mimics the effect of root exudate on reversing the delay in the initiation of infection. As a control, preincubation of strain HS111 in (10 μg/ml) bovine serum albumin (BSA) did not enhance the nodulating properties of strain HS111.

EXAMPLE III

A series of experiments were conducted to further demonstrate that the nodulation enhancement factor found in soybean root exudate is a lectin with similar properties to that of soybean seed lectin. In these experiments, soybean root exudate obtained by the procedure of Example I was passed through a sepharose-n-caproyl galactosamine affinity column as follows:

A. Preparation of Sepharose-N-Caproyl Galactosamine Affinity Column

The sepharose-n-caproyl galactosamine was prepared by the method of Allen, A. K. and Neuberger, A. (1975) FEBS LETT. 50:362-363.

B. Affinity Column Treatment of Root Exudate

The gel was poured in a 10 ml plasti-pak disposable syringe plugged with a siliconized glass fiber and washed with 100 ml PBS. Root exudate was prepared as described previously and 120 ml of root exudate was passed through the column three times (hereafter referred to as Affinity Eluate). Affinity Eluate was filter sterilized and stored at 4° C. The column was washed with 100 ml PBS and the lectin eluted with 50 ml of 200 mM D-galactose suspended in PBS. The eluted lectin (Affinity Lectin) was monitored by absorbance at 280 nm. Affinity Lectin was dialyzed extensively over a 24 h period against distilled H$_2$O. The dialyzed lectin was resuspended to a volume of 120 ml with sterile half-strength PNS and filter-sterilized.

The mutant strain HS111 was preincubated with the Affinity Eluate, Affinity Lectin, PNS and RE for 72 h prior to inoculation of 3 day old seedlings with a cell concentration of approximately 1×10$^8$ cells per ml. Inoculation of the seedlings were performed as described in Example I.

The slow to nodulate mutants were scored after 28 days of growth. The results are set forth in the following Table IV.

TABLE IV

| Pretreatment | Average Distance of Uppermost Nodule From RT (mm) | % Nodulation Only Below RT Mark |
|---|---|---|
| PNS | −14.8 ± 4.0 | 70 |
| Affinity Eluate | −13.8 ± 2.4 | 63 |
| RE | −1.3 ± 1.3 | 31 |
| Affinity Lectin | −1.1 ± 1.1 | 37 |

As shown in Table IV, preincubation of mutant strain HS111 with the Affinity Lectin results in nodulation characteristics similar to that exhibited by preincubation in soybean root exudate. Preincubation of mutant strain HS111 in Affinity Eluate (soybean root exudate with SBL removed by affinity chromatography) exhibits nodulation characteristics similar to that seen by preincubation of strain HS111 in sterile half-strength PNS. Affinity column treatment of soybean root exudate obtained from G. max CV. Essex and inoculated onto G. max CV. Forrest resulted in a similar response (data not shown).

EXAMPLE IV

A series of experiments were carried out to demonstrate the effect of treatment with soybean root exudate on the nodulation characteristic of *Rhizobium japonicum* strains having elevated, normal and depressed nodulation phenotypes. Root exudate from aseptically grown Essex soybean grown hydroponically for 10 days in Plant Nutrient Solution (PNS) was isolated using the procedure as described by Halverson and Stacey, 1984—Host recognition in the Rhizobium—soybean symbiosis. *Plant Physiol.* 74:84–89, (1984). *Rhizobium japonicum* strains Tn119, I-110 and HS111 (representing elevated, normal and depressed nodulation phenotypes, respectively) were utilized for root exudate treatment. These strains were grown on YEM broth till midexponential phase (4 days), cells were harvested by centrifugation for 10 min at 6,000 rpm. Cell pellets from 100 ml of culture were resuspended in either 60 ml of PNS or soybean root exudate (RE), and incubated for 48 hours under static conditions at ambient temperature. Cell counts following treatment were determined microscopically utilizing a hanocylometer. Cell counts of these suspensions are set forth below in Table V

TABLE V

| | Cells per 1 ml of Suspension | |
|---|---|---|
| Strain | PNS | RE |
| I-110 | 1.25 × 10$^9$ | 1.53 × 10$^9$ |
| HS111 | 1.08 × 10$^9$ | 1.46 × 10$^9$ |
| Tr119 | 1.52 × 10$^9$ | 2.05 × 10$^9$ |

As is apparent from Table V, similar populations of rhizobial cells were present in each suspension, thus, indicating the influence of root exudate is not on enhancing rhizobial growth.

Plant test

The rhizobial suspensions of Table V were evaluated as inoculants in a plant test as follows. Plant growth containers were made by modifying Leonard jar assemblies as typically done by those skilled in the art. Styrefoam cups (500 mL capacity) were filled with approximately 400 ml of sterile sand vermiculite mixture (50:50 volume:volume). For the lower reservoir a 250 ml capacity styrefoam cup is utilized. A rope wick 6–8 cm is inserted through a hole in the center of the upper cup. To the reservoir is added 150 ml of nitrogen free nutrient solution. Four surface sterilized soybean seeds (Essex cv) were planted per Leonard jar assembly. Seeds were inoculated with 0.5 ml of suspensions pipetted directly over the seeds. Inoculated seeds were covered with an additional layer of sand vermiculite and a thin layer of paraffin coated sand to minimize contamination. Six replicate jars were utilized for each treatment including six replicate uninoculated jars.

Seven days after planting, seedlings were removed to achieve two plants per replicate. Plants were grown for 35 days after which nodulation counts were determined visually. The results of this experiment are set forth in the following Table VI.

TABLE VI

| Rhizobial strain | Nodule No Per Plant | |
|---|---|---|
| | PNS | RE |
| HS111 | 7 ± 2 | 49 ± 12 |
| I-110 | 12 ± 1 | 37 ± 2 |
| TN119 | 17 ± 3 | 48 ± 18 |

As shown in Table VI, in the absence of root exudate treatment typical nodulation phenotypes were observed, HS-111 (depressed nodulation), I-110 (moderate nodulation) and Tn 119 (elevated nodulation). Unincubated control plants exhibited no nodulation. Soybeans inoculated with root exudate pretreated inoculant exhibited enhanced nodulation of 3 to 9 fold of that of controls of Table VI. The level of enhanced nodulation is similar regardless of nodulation phenotypes, thus a slow to nodulate mutant is capable of attaining nodulations comparable to rapidly nodulating mutants.

EXAMPLE V

A series of experiments were carried out to evaluate the effects of treatment, with soybean root exudate on the competitiveness of characteristics of *Rhizobium japonicum* strains having elevated, normal and depressed nodulation characteristics. In these experiments, an additional strain of *R. japonicum*, USDA 122 was used as the competing strain of *R. japonicum*. The test suspension were formed by addition of YEMB cultures of USDA 122 containing approximtely 2×10$^9$ cells for mL to either PNS or RE conditioned suspensions of strains Tn119, I-110 and HS111 described in Table V. These test suspensions were evaluated in a plant test using the procedure of EXAMPLE V. After 35 days of plant growth nodules were collected and stored at −5° C. for nodule occupancy determinations. The presence of 110 sero group (strains Tn119, I-110 and HS111 all belong to this group) as a nodule occupant was determined utilizing the ELISA (Enzyme Linked Immunoabsorbant Assay), Kishinensky and Cusut, *Microbiology*, 9:45 (1983).

The results of these experiments are set forth in the following Table VIII.

TABLE VIII

| Base Strain | No. of Individual Members of Base Strain | | % Increase In Occupancy |
| --- | --- | --- | --- |
| | PNS | RE | |
| I-110 | 26 | 41 | 56 |
| Tn119 | 23 | 40 | 74 |
| HS111 | 14 | 32 | 128 |

As shown in Table VII, an important benefit of root exudate treatment is increased competitiveness. Suspensions of all three strains in root exudate exhibited a 56% to 128% increase in nodule occupancy when challenged with a ninefold higher population of untreated strain USDA 122. As is demonstrated in Table VIII, it is evident that increases of nodulation attributable to root exudate treatment can also enhance the competitiveness of the treated cells.

EXAMPLE VII

I. Materials and Methods

A. Rhizobium Cultures and Plant Varieties

*Rhizobium japonicum* wild type strain 311b110 is colony type I110. Isolation of mutant strains HS111 and HS123, and partial characterization of their nodulation phenotype was reported previously in Stacey G. et al., "Mutants of *Rhizobium japonicum* Defective in Nodulation", *Arch Microbiol*, 132:219-2240 (1982). The soybean (Glycine max L. Merr) cultivars Essex, Forrest and Ransom were obtained from D. R. Mayo Seed Co., Knoxville, Tenn. *Glycine soja* and *Glycine max* cultivar T102 (lacking seed lectin), were originally obtained from T. Hymowitz (University of Illinois Urbana, Ill.). The seed supply for cultivar T102 was increased by growth of plants in a greenhouse in which no other soybean plants were grown. Seeds were tested for the presence of seed lectin before use by removing and grinding the cotyledons of seedlings 2 days after germination in 1 ml of a phosphate buffered saline (PBS, 6.8 g $KH_2PO_4$, 8.7 g $K_2HPO_4$ and 8.7 g NaCl per liter distilled $H_2O$). After extraction with PBS overnight, the seed extract was tested for the presence of seed lectin by Ouchterlony double diffusion against anti-seed lectin antibody. This method gave a precipitant band when tested against the lectin containing cultivar Essex but no precipitant band was seen with the cultivar T102 seeds.

B. Preparation of Rhizobium Inocula

Single colonies from YEM agar stock cultures were used to inoculate 50 ml of YEM both in 250 ml Erlenmeyer flasks. These cultures were maintained on a rotary shaker at 30° C. for 3.5 days (midlog phase). Cultures were harvested by centrifugation at 7,000× g for 10 min in sterile sucrose-free half-strength Plant Nutrient Solution (PNS), and suspended in sterile half-strength PNS to a cell density of either $1 \times 10^8$ cells/ml or $2 \times 10^9$ cells/ml. Aliquots of such suspensions were used to inoculate plants directly ($1 \times 10^8$ cells/ml) or for pretreatment inoculations ($2 \times 10^9$ cells/ml) as described in Example I.

C. Growth of Seedlings and Collection of Root Exudates

Seeds were surface sterilized and germinated as described previously in Example I. Seedlings were transferred aseptically to clear plastic growth pouches (diSPo Seed Pack, Northrup King Seed Co.). Seedlings were maintained in a growth chamber under the following conditions: 26° C., light intensity 320 $\mu E\ m^{-2} sec^{-1}$ with a 14 h photoperiod. The plastic pouches were watered as needed with sterile half-strength PNS. Root exudate was obtained as described previously in Example I.

D. Rhizobium Pretreatments and Inoculation of Plants

*R. japonicum* cultures were prepared as described above. Ten ml of the $2 \times 10^9$ cells/ml suspensions were aseptically added to 50 ml of root exudate or PNS in 250 ml Erlenmeyer flasks and incubated at 30° C. without shaking for 1 to 72 h. Following the desired incubation time, the cell suspension was pelletized in sterile centrifuge tubes at 7,000 g for 10 min, washed once with sterile half-strength PNS, and resuspended to the original volume with PNS or for the binding experiments to a concentration of approximately $2 \times 10^9$ cells/ml.

The position of the root tip (RT) and smallest emerging root hair (SERH) of 3 day old seedlings were marked on the surface of the growth pouches with the aid of a dissecting microscope as described previously in Example I. The entire root of each seedling was inoculated with 1.0 ml of a $1 \times 10^8$ cells/ml suspension.

E. Nodule Scoring

Plants inoculated with the wild type *R. japonicum* strain were scored 28 days after inoculation and the slow-to-nodulate mutant strain HS111 was scored 28 days after inoculation. The position of all nodules on the primary root was measured relative to the RT mark made at the time of inoculation to the nearest 0.1 mm as described in Example I.

II. RESULTS

A. Nodulation Enhancement by a "Lectinless" Soybean Line T102

Lines of soybean have been isolated which possess a genetic insertion in the structural gene encoding the soybean lectin (Orf. JH "Inheritance of Soybean Seed Lectin", *Crop Science*, 102:380-391 (1978). These lines lacking detectable seed lectin are nodulated by strains of *R. japonicum* and, therefore, represent a challenge to the postulated essential role of a lectin in nodulation. Soybean root exudate from one of these lines, T102, was tested for its effect on the nodulation characteristics of mutant strain HS111. In these experiments, root exudate from Glycine Max T102 was isolated using the procedure of paragraph I (C). Seeds of this variety were grown under quarantine conditions in the greenhouse to prevent outcrossing and checked for seed lectin before use through use of Ouchterlony double diffusion against anti-seed lectin antibody as described in paragraph I (A) above. As described in paragraph I (D), cultures of *R. japonicum* strain HS111 were aseptically added to the T102 root exudate or PNS and incubated for 72 h. Afterwards, these suspensions were used to inoculate 33 to 37 plants of G. Max cv. Essex with 1 ml of an approximate Rhizobium cell concentration of $1 \times 10^8$ cells/ml. The inoculated plants were then scored using the procedure of paragraph I (E). The results of these experiments are set forth in the following Table IX.

TABLE IX

Nodulation Characteristics of Strain HS111 Pretreated With Root Exudate (RE) Obtained from the Lectinless Line Glycine Max T102

| Pretreatment | Average Distance of Uppermost Nodule From RT Mark (mm) | % Nodulation Only Below RT Mark |
| --- | --- | --- |
| PNS | −18.5 ± 3.7 | 64 |
| T102 RE | −0.7 ± 1.3 | 46 |

As is apparent from the data in Table IX, RE from Glycine Max T102 enhanced nodulation of strain HS111 in an identical fashion to that obtained from other varieties. The average distance of the uppermost nodule from the RT mark after preincubation in T102 RE is 0.7±2.3 mm below the RT mark. These results suggest that there are other lectins in the soybean root which differ from soybean seed lectin and which also have a beneficial effect on nodulation.

B. Lectin Titration

Preincubation of the slow-to-nodulate mutant strain HS111 in soybean seed lectin (SBL) as described in Example I was done at a concentration of 10 μg SBL/ml the approximate total protein concentration of soybean root exudate. This concentration is most likely greater than the lectin concentration found in soybean root exudate. To determine the number of soybean lectin molecules necessary for nodulation enhancement, mutant strain HS111 was preincubated in various concentrations of soybean seed lectin using the above referenced procedures and the effect of such preincubation on the position of the nodules is noted. In these experiments, strain HS111 was pretreated for 72 h in soybean seed lectin (SBL) at concentrations ranging from 1 to $2.5 \times 10^8$ molecules of SBL/cell, or 10 μg of SBL/ml, the same concentration of SBL used in the previous experiments. Following pretreatment, the cells were pelleted, washed and resuspended in PNS for inoculation of 3 day old seedlings of G. Max cv Essex with an approximate cell concentration of $1 \times 10^8$ cells/ml.

The results are set forth in the following Table X.

TABLE X

Effect of Various Concentrations of SBL on the Nodulation Enhancement of Mutant Strain HS111

| Pretreatment | Molecules SBL per cell | Average Distance of Uppermost Nodule from RT Mark (mm) | % Nodulation Only Below RT |
| --- | --- | --- | --- |
| PNS | 0 | −18.8 ± 3.2 | 84 |
| SBL | 1 | −15.6 ± 3.2 | 83 |
| SBL | 10 | −19.2 ± 3.5 | 86 |
| SBL | 100 | −12.0 ± 3.1 | 64 |
| SBL | $1 \times 10^4$ | −5.9 ± 1.9 | 64 |
| SBL | $1 \times 10^6$ | −0.4 ± 1.9 | 60 |
| SBL | $2.5 \times 10^8$ | −0.4 ± 1.4 | 33 |

Pretreatment of strain HS111 at a concentration of 1 or 10 molecules SBL per cell does not include a measurable physiological response for nodulation enhancement of mutant strain HS111. However, at a concentration of 100 molecules SBL per cell there is a slight response in nodulation enhancement of strain HS111 where the average distance of the uppermost nodule is 12.0±3.1 mm below the RT mark. A significant response is evident at a concentration of $1 \times 10^4$ molecules of SBL per cell. In this case the average distance of the uppermost nodule is 5.9±1.9 mm below the RT mark. At a concentration of $1 \times 10^6$ molecules SBL per cell the nodulation response is comparable to that exhibited by strain HS111 at a concentration of $2.5 \times 10^8$ molecules SBL per cell. Therefore, the data indicate that strain HS111's physiological response of nodulation enhancement due to lectin pretreatment occurs at a concentration between 100 and 10,000 molecules/cell as measured by this bioassay.

C. Pretreatment Time on Nodulation Enhancement

To deduce the amount of time necessary for strain HS111 to interact with SBL for nodulation enhancement to occur the following experiments were performed. First, strain HS111 was pretreated with 10 ug of SBL/ml for 1 h, pelleted, washed, resuspended in sterile, half-strength PNS to the original volume, and incubated for the duration of the 72 h preincubation period prior to inoculation of 3 day old seedlings of G. max cv. Essex with an approximate cell concentration of $1 \times 10^8$ cells/ml. In addition strain HS111 was pretreated for 0 or 1 hr in 10 ug of SBL/ml, pelleted, washed and resuspended sterile half-strength PNS and used to inoculate 3 day old seedlings with an approximate cell concentration of $1 \times 10^8$ cells/ml. The plant nodules were scored after 28 days of growth. The results are set forth in the following Table XI.

TABLE XI

Effect of SBL Preincubation Time on the Nodulation Enhancement of Mutant Strain HS111

| Pretreatment | Time of Incubation (h) | Average Distance of Uppermost Nodule from RT Mark (mm) | % Nodulation Only Below RT |
| --- | --- | --- | --- |
| PNS[a] | 1 + 71 | −15.7 ± 4.7[d] | 71 |
| SBL[b] | 0 | −17.7 ± 3.9 | 78 |
| SBL[b] | 1 | −17.8 ± 3.2 | 72 |
| SBL[a] | 1 + 71 | −11.1 ± 4.8 | 48 |

[a]Strain HS111 was pretreated for 1 h, pelleted, washed and resuspended in sterile half-strength PNS and incubated for the duration of the 72 h preincubation period prior to inoculation of 3 day old seedlings with an approximate cell concentration of $1 \times 10^8$ cells/ml.
[b]Strain HS111 was pretreated for 0 or 1 h, pelleted, washed and resuspended in sterile half-strength PNS and used to inoculate 3 day old seedlings with an approximate cell concentration of $1 \times 10^8$ cells/ml.

Under SBL pretreatment conditions of 0 to 1 h, strain HS111's nodulation response is comparable to that seen for strain HS111 pretreated in sterile half-strength PNS alone. However, if the cells are pretreated in SBL for 1 h, pelleted, washed and resuspended in sterile half-strength PNS and incubated for the duration of the 72 h incubation period a significant change in strain HS111's nodulation response is detected. These data indicate that strain HS111 interacts with the lectin within an hour, however, the physiological response necessary for nodulation enhancement does not occur immediately.

D. Nodulation Characteristics of Strains 3I1b110 and HS111 with Various Soybean Cultivars To determine if the nodulation characteristics exhibited by the wild type R. japonicum strain 3I1b110 and the slow-to-nodulate mutant strain HS111 are not specific to the cultivar Essex, the nodulation characteristics of strain 3I1b110 and HS111 were examined using other soybean cultivars Glycine max (L.) Merr cv Ransom (Ransom), Glycine max (L) Merr. cv Forest (Forest) and Glycine soja (Soja). In these experiments, various Rhizobia were preincubated in PNS for 72 h prior to inoculation or in soybean root exudate obtained from cultivars Ransom (Ransom RE), Essex (Essex RE) and Forrest (Forrest RE) for 72 h prior to inoculation.

Thereafter, the sets of from 34–53 (3) day old plants were inoculated with 1 ml of an approximate Rhizobium cell concentration of $1 \times 10^8$ cells per ml. After 28 day growth the plants were scored. The results are set forth in the following Tables XH and XIII.

TABLE XII

Nodulation Characteristics of *R. japonicum* Strain 3Ilb110 and the Mutant Strain HS111 With Various Cultivars

| | | | |
|---|---|---|---|
| 1) Strain | | 3Ilb110 | |
| 2) Pretreatment | | NONE | |
| 3) Cultivar Treated | Ransom | Forrest | Soja |
| 4) Average Distance of Uppermost Nodule From RT mark (mm) | 3.5 ± 0.7 | 2.4 ± 1.7 | 20.0 ± 1.7 |
| 5) % Nodulation Only Below RT Mark | 14 | 28 | 4 |
| 1) Strain | | HS111 | |
| 2) Pretreatment | | PNS | |
| 3) Cultivar Treated | Ransom | Forrest | Soja |
| 4) Average Distance of Uppermost Nodule From RT mark (mm) | −10.0 ± 3.5 | −12.9 ± 1.9 | −28.0 ± 3.5 |
| 5) % Nodulation Only Below RT Mark | 71 | 74 | 93 |
| 1) Strain | | HS111 | |
| 2) Pretreatment | | Essex RE | |
| 3) Cultivar Treated | Ransom | Forrest | Soya |
| Average Distance of Uppermost Nodule From RT mark (mm) | 2.6 ± 1.0 | 1.3 ± 1.3 | −3.1 ± 1.3 |
| 5) % Nodulation Only Below RT Mark | 26 | 33 | 47 |

TABLE XIII

Nodulation Characteristics of Mutant Strain HS111 Pretreated with Root Exudate Obtained From Cultivars Ransom and Forrest.

| Pretreatment | Cultivar Treated | Average Distance of Uppermost Nodule from RT Mark (mm) | % Nodulation Only Below RT Mark |
|---|---|---|---|
| Ransom | | | |
| RE | Ransom | −1.7 ± 2.4 | 23 |
| PNS | Ransom | −11.7 ± 2.9 | 73 |
| Ransom | | | |
| RE | Essex | −1.8 ± 1.6 | 31 |
| PNS | Essex | −17.9 ± 3.2 | 80 |
| Forrest | | | |
| RE | Forrest | −1.2 ± 1.9 | 32 |
| PNS | Forrest | 13.2 ± 2.3 | 70 |
| Forrest | | | |
| RE | Essex | −1.0 ± 1.5 | 31 |
| PNS | Essex | −16.5 ± 4.1 | 68 |

Table XII shows the nodulation characteristics of *R. japonicum* strain 110 and strain HS111 with the commercial soybean cultivars Ransom and Forrest, and the wild, ancestral soybean *Glycine soja*. The average distance of the uppermost nodule, for strain 3Ilb110, was 3.5±0.7, 2.4±1.7 and 20.0±1.7 mm above the RT mark made at the time of inoculation for cultivars Ransom, Forrest and *G. soja*, respectively (Table XII). The percentage of plants nodulating with strain 3Ilb110 only below the RT mark for the cultivars Ransom, Forrest, and *G. soja* were 14, 28 and 4%, respectively (Table XII). The commercial soybean cultivars Ransom and Forrest nodulated similar to the commercial cultivar Essex when inoculated with the wild type *R. japonicum* strain 110. However, the non-commercial soybean *Glycine soja* nodulated in an area outside of the RT-SERH area. The reason for this unique nodulation with *G. soja* is unknown.

Inoculation of the soybean cultivars Ransom and Forrest with the slow-to-nodulate mutant strain HS111 resulted in the average distance of the uppermost nodule being 10.0±3.5 and 12.9±1.9 mm below the RT mark respectively (Table XIII). Seventy-one percent and 74% of the plants nodulated only below the RT mark made at the time of inoculation for cultivars Ransom and Forrest, respectively (Table XIII). Inoculation of *G. soja* with strain HS111 resulted in 93% of the plants nodulating only below the RT mark with the average distance of the uppermost nodule being 28.0±3.5 mm below the RT mark made at the time of inoculation. Therefore, strain HS111's nodulation phenotype is not restricted to the soybean cultivar Essex.

Preincubation of strain HS111 in root exudates, obtained from the soybean cultivars Essex, prior to inoculation of the soybean cultivars Ransom and Forrest resulted in a reversal of strain HS111's delay in the initiation of nodulation phenotype (Tables XII and XIII). The average distance of the uppermost nodule from the RT mark for the cultivars Ransom and Forrest, respectively, were 2.6±1.0 and 1.3±1.3 mm above the RT mark with 26 and 33% of the plants nodulating only below the RT mark made at the time of inoculation (Table XII). These data in Table XII and XIII demonstrate that preincubation of strain HS111 in soybean RE obtained from the cultivars Forrest, Essex and Ransom have the capability of enhancing strain HS111's nodulation characteristics. This indicates that the factor(s) found in soybean root exudate which enhances the nodulation characteristics of strain HS111 are not unique to any one cultivar.

D. Preincubation in Cowpea Root Exudate

*Rhizobium japonicum* is capable of nodulating cowpea (*Vigna unguiculata* L. Walp) and therefore does not follow the classical definition of cross-inoculation groups. Certain experiments were conducted to determine if root exudates obtained from cowpea had the same effects as soybean root exudates on the nodulation characteristics of strain HS111. In these experiments, strain HS111 was pretreated for 72 h in PNS or RE obtained from cowpea (*Vigna ungicultata* L. Walp) cultivar Mississippi Silver Hull prior to inoculation of 3 day old *G. max* cultivar Essex seedlings with a cell concentration of approximately $1 \times 10^8$ cells/ml. The sets of 32–49 plants were scored for nodulation 28 days after inoculation. The results are set forth in the following Table XIV.

TABLE XIV

Effect of Cowpea (*Vigna unquiculata* L. Walp) Root Exudate on the Nodulation Characteristics of Strain HS111.

| Treatment | Average Distance of Uppermost Nodule from RT Mark (mm) | % Nodulation Only Below RT |
|---|---|---|
| PNS | −21.2 ± 4.0 | 75 |
| RE | −20.3 ± 2.5 | 81 |

The data in Table XIV demonstrate that preincubation of strain HS111 in cowpea root exudate does not result in the enhancement of the initiation of nodulation by strain HS111 unlike soybean root exudate. The average distance of the uppermost nodule from the RT mark for strain HS111 preincubated in sterile half-strength PNS and cowpea root exudate, respectively, was 21.2±4.0 and 20.3±2.5 mm below the RT mark with 75 and 81% of the plants nodulating only below the RT mark made at the time of inoculation.

E. Double Inoculation Experiment

To determine if strain HS111 induces a host plant response which inhibits nodulation by strain HS111 a double inoculation experiment was performed. Three day old seedlings of G. max cv Essex were inoculated with $1 \times 10^8$ cells/ml of the slow-to-nodulate mutant which was preincubated in sterile half-strength PNS, with or without soybean lectin (SBL) (10 μg/ml). One hour later the seedlings were inoculated with $1 \times 10^8$ cells/ml of a wild type strain of 3Ilb110 which was resistant to 100 ug/ml Streptomycin (3Ilb110 StrR). In another set of experiments seedlings were inoculated with $1 \times 10^8$ cells/ml of an equal mixture of the mutant strain HS111 and the streptomycin resistant strain of 3Ilb110. Plants were scored for nodulation 28 days after inoculation. Rhizobium were isolated from the nodules as described previously. Nodule isolates were streaked onto YEM agar and incubated at 30° C. Single colony isolates were first streaked onto YEM agar containing 100 ug/ml streptomycin then onto YEM agar which did not contain any antibiotic. Following pretreatment, in SBL (10 ug/ml) or sterile half-strength PNS for 72 h prior to inoculation strain HS111 was either mixed with an equal volume of the wild type strain 3Ilb110 resistant to 100 ug/ml streptomycin or the same plant was inoculated 1 h later. This experiment was performed based on the hypothesis that if strain HS111 induces a host response preventing nodulation then the 3Ilb110 StrR challenge inoculum should not induce nodule formation. However, if pretreatment in SBL inhibits strain HS111 ability to induce a host plant response preventing nodulation, the nodules near the RT mark should contain a mixed population of strain 3Ilb110 and HS111. The results of this experiment are set forth in the following Table XV.

TABLE XV

Competition for Nodulation Between the Wild Type Strain 3Ilb110 and the Slow-to-Nodulate Mutant Strain HS111.

| Pretreatment | Average Distance of Uppermost Nodule from RT Mark (mm) | % Nodulation Only Below RT Mark |
|---|---|---|
| A. Mix Inoculum | | |
| PNS 3Ilb110 | −0.1 ± 0.9 | 39 |
| HS111 PNS + PNS | −17.1 ± 3.6 | 76 |
| HS111 SBL + PNS | −2.6 ± 2.5 | 38 |
| HS111 PNS + 3Ilb110 | −1.9 ± 1.3 | 40 |
| HS111 SBL + 3Ilb110 | −0.5 ± 1.7 | 35 |
| B. 1 h Delay | | |
| 1st        2nd | | |
| HS111 SBL   PNS | −1.7 ± 1.9 | 40 |
| HS111 PNS   PNS | −19.0 ± 4.8 | 79 |
| HS111 SBL   3Ilb110 Str | −3.0 ± 1.3 | 49 |
| HS111 PNS   3Ilb110 Str | −3.2 ± 2.9 | 45 |

In Table XV it is evident that strain HS111 preincubated in PNS does not induce a host plant response which inhibits nodulation. The lack of this response is seen using both a mixed inoculum and a 1 h delay challenge inoculation since the average distance of the uppermost nodule is near the RT mark for both cases. Bacteria were isolated from the nodules to determine which strain of Rhizobium nodulated near the RT mark. The streptomycin marker found in the wild type strain 3Ilb110 provided a means to determine which strain formed the nodules. In the case of bacteria isolated from plants from the mixed inoculation experiment where HS111 PNS was challenged with 3Ilb110 Str, 100% of the colonies isolated where the wild type. However, 93% of the colonies checked for antibiotic resistance in the mixed HS111 SBL and 3Ilb110 Str experiment were strain 3Ilb110 indicating that in both cases the wild type had a competitive advantage over the mutant.

F. Root Binding Experiment

This experiment was performed to determine if preincubation of strain HS111 in SBL or RE increases or induces binding to the plant root. In these experiments, Rhizobium cultures were prepared as described previously. Three day old seedlings of G. max cv. Essex were suspended atop a sterilized Nestrite cup (Lily-Tulip Division of Owens-Illinois, Toledo, Ohio) containing 230 ml of a $1 \times 10^8$ cells/ml Rhizobium suspension and allowed to incubate at room temperature for 1 h. Following the 1 h inoculation period the seedlings were washed by placing the seedlings atop of another Nestrite cup containing 230 ml of sterile half-strength PNS and shaking for 15 min on a Queu rotary shaker at 75 rpm. Washes were performed one to six times. After the appropriate wash the distal 20 mm segment of the root was excised and tissue homogenized with 1.0 ml of sterile half-strength PNS. Quantitation of the number of bacteria bound to the root segment was determined by serial dilutions of the homogenized root cell suspension. As a preliminary step it was first necessary to determine the minimum number of washes necessary to remove non-specific binding. It was found that after three washes no additional Rhizobium cells are removed by subsequent washing. Results work suggests that preincubation of strain HS111 in SBL or RE does not enhance binding of strain HS111 to the plant root. As a negative control, results also indicate that the nonbinding mutant strain HS111 binds to the soybean root at a rate 2-3 magnitudes less than the wild type strain.

What is claimed is:

1. A method for preparing a composition for enhancing soybean nodulation which comprises:
   contacting a strain of the species Rhizobium japonicum with a nodulation-enhancing effective amount of a soybean seed lectin;
   incubating said strain in an aqueous liquid for at least about one hour under conditions effective to enhance the nodulation characteristics of said strain;
   then recovering and purifying cells of said strain;
   then suspending said cells in a lectin-free aqueous medium; and
   then reincubating said cells for a period sufficient to further enhance nodulation characteristics of said cells of said strain.

2. The method of claim 1 wherein said cells are purified by pelleting and washing, said aqueous medium comprises a plant nutrient solution, and the total incubation time for both said incubation and reincubation steps is at least about 72 hours.

* * * * *

UNITED STATES PATENT AND TRADEMARK OFFICE
CERTIFICATE OF CORRECTION

PATENT NO. : 5,173,424

DATED : December 22, 1992

INVENTOR(S) : Stacey et al.

It is certified that error appears in the above-identified patent and that said Letters Patent is hereby corrected as shown below:

In the Title, Field [54], change "MODULATION" to

-- NODULATION --.

Signed and Sealed this

Twenty-fifth Day of January, 1994

Attest:

BRUCE LEHMAN

Attesting Officer     *Commissioner of Patents and Trademarks*